US00PP26213P3

(12) United States Plant Patent
Growns

(10) Patent No.: US PP26,213 P3
(45) Date of Patent: Dec. 15, 2015

(54) WAXFLOWER PLANT NAMED 'WX 87'

(50) Latin Name: ***Chamelaucium* hybrid (*Chamelaucium uncinatum*×*Chamelaucium megalopetalum*)**
Varietal Denomination: WX 87

(71) Applicant: Western Australian Agriculture Authority, Bentley (AU)

(72) Inventor: Digby Growns, Kings Park (AU)

(73) Assignee: Western Australian Agriculture Authority, Bentley (AU)

( * ) Notice: Subject to any disclaimer, the term of this patent is extended or adjusted under 35 U.S.C. 154(b) by 143 days.

(21) Appl. No.: 13/987,930

(22) Filed: Sep. 16, 2013

(65) Prior Publication Data

US 2014/0082790 P1 Mar. 20, 2014

Related U.S. Application Data

(60) Provisional application No. 61/744,179, filed on Sep. 19, 2012.

(51) Int. Cl.
*A01H 5/02* (2006.01)

(52) U.S. Cl.
USPC ..... Plt./229
CPC ..... *A01H 5/02* (2013.01)

(58) Field of Classification Search
USPC ..... Plt./226, 229
See application file for complete search history.

(56) References Cited

PUBLICATIONS van der Ploeg, R., "Exciting developments in waxflower breeding and marketing," Sep. 2011; www.FloraCultureInternational.com—file retrieval on Mar. 28, 2015 (3 pages total).*
www.wafex.com.au/pages/about_wafex/news/2011-09; summary of "Exciting developments in waxflower breeding and marketing," Monday, Sep. 5, 2011; file retrieval on Mar. 30, 2015 (1 page total).*
"New waxflower varieties released," Australian Flower Industry; Sep. 2011; file retrieval on Mar. 30, 2015 (1 page total).*
www.wafex.com.au/pages/about_wafex/news/2011-09; summary of "New waxflower varieties released," Thursday, Sep. 1, 2011; file retrieval on Mar. 30, 2015 (1 page total).*

* cited by examiner

*Primary Examiner* — Susan McCormick Ewoldt
(74) *Attorney, Agent, or Firm* — Michelle Bos Legal LLC

(57) ABSTRACT

'WX 87' is a new and distinct waxflower plant (interspecific *Chamelaucium* hybrid) notable for its very late flowering, compact growth habit, and dense terminal cover of large white flowers that age to white with green-yellow hypanthium.

5 Drawing Sheets

Latin name of the genus and species of the plant claimed: Interspecific *Chamelaucium* hybrid (*Chamelaucium uncinatum*×*Chamelaucium megalopetalum*).

Variety denomination: 'WX 87'.

BACKGROUND OF THE INVENTION

'WX 87' is a new waxflower plant that originated as a seedling produced in a sexual breeding program conducted by the breeder at Medina and South Perth, Western Australia. 'WX 87' was selected from seedlings of a controlled pollination of female parent *Chamelaucium uncinatum* 'BP Pale' (not patented) by male parent *C. megalopetalum* 'CM 11.1' (not patented) at Medina, Western Australia. An embryo was excised from fruit produced in November 2001 and germinated in vitro. The resulting seedling was subcultured in tissue culture four times, deflasked, hardened and planted in the field at Medina, Western Australia in July 2002. Following flowering in July 2003, the seedling was vegetatively propagated via cuttings and a second generation of cuttings was taken in 2009 at Medina, Western Australia. Growth and flowering records of the generations were recorded from 2003 to 2010. No off-types were recorded and all plants were found to be uniform and stable.

'WX 87' is distinguishable from its female parent 'BP Pale' by a number of features, as described in Table 1 below:

TABLE 1

| Characteristic | BP Pale | WX 87 |
|---|---|---|
| Flower colour | Pale purple to purple | White |
| Leaf cross-section | Rounded | Flattened triangular |
| Flower: attitude of petals | Horizontal | Semi-erect to erect |
| Flower: colour of hypanthium | Pink-purple | Yellow |

'WX 87' is distinguishable from its male parent 'CM11.1' by a number of features, as described in Table 2 below:

TABLE 2

| Characteristic | CM11.1 | WX 87 |
|---|---|---|
| Leaf length | Short | Medium |
| Plant height | Short | Medium-tall |
| Flower diameter | Large | Medium |

'WX 87' is also distinguishable from other known waxflower varieties. Comparisons of 'WX 87' to 'Ivory Pearl'

(not patented) and 'WX 74' (patent pending), the most similar varieties of common knowledge, are set forth in Tables 3 and 4 below:

TABLE 3

| Characteristic | Ivory Pearl | WX 87 |
|---|---|---|
| Leaf length | Long | Short |
| Leaf cross-section | Round | Flattened/triangular |
| Pedicel length | Medium to long | Short to medium |
| Flower diameter | Medium to large | Medium |

TABLE 4

| Characteristic | WX 74 | WX 87 |
|---|---|---|
| Leaf length | Short to medium | Medium |
| Flower: color of hypanthium | Yellow-green | Yellow |
| Calyx tube furrowing | Weak | Medium |
| Time of beginning of flowering | Medium | Medium to late |

BRIEF DESCRIPTION OF THE PHOTOGRAPH

The accompanying photographs show four-year-old 'WX 74' waxflower plants growing at Medina, Western Australia during August and September (early spring) 2013.

DETAILED BOTANICAL DESCRIPTION

Figure 1:
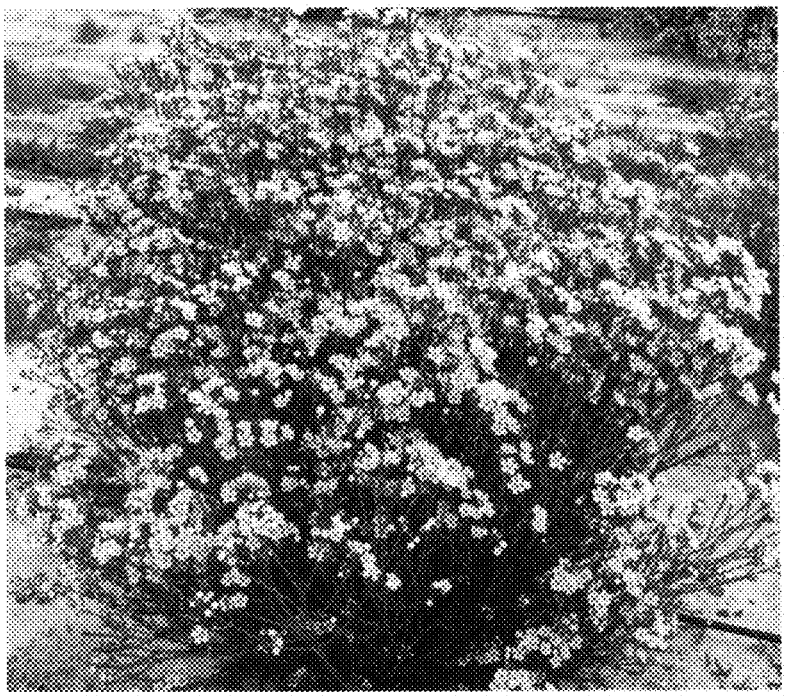
FIG. 1 is a photograph of 'WX 87' growing outdoors.
Figure 2:
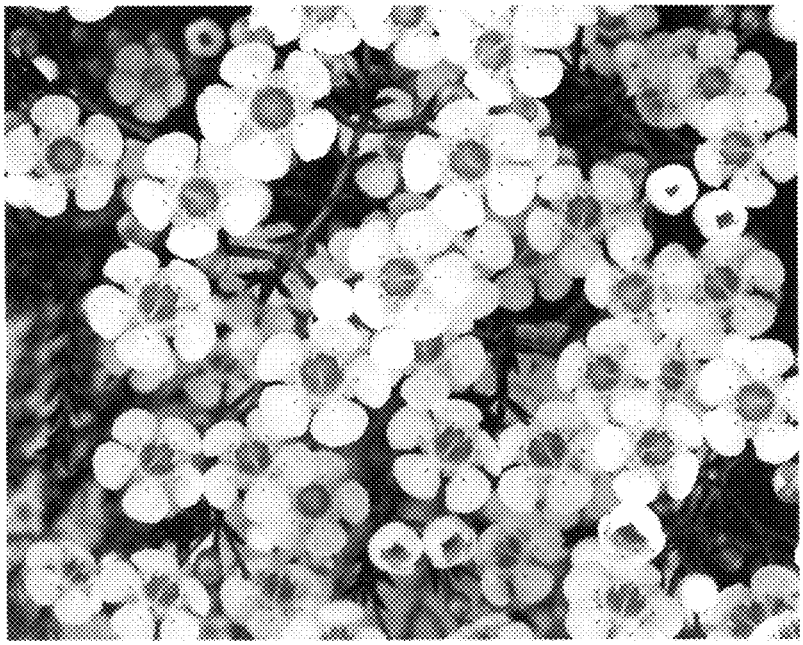
FIG. 2 is a close-up photograph of young flowers of 'WX 87'.
Figure 3:
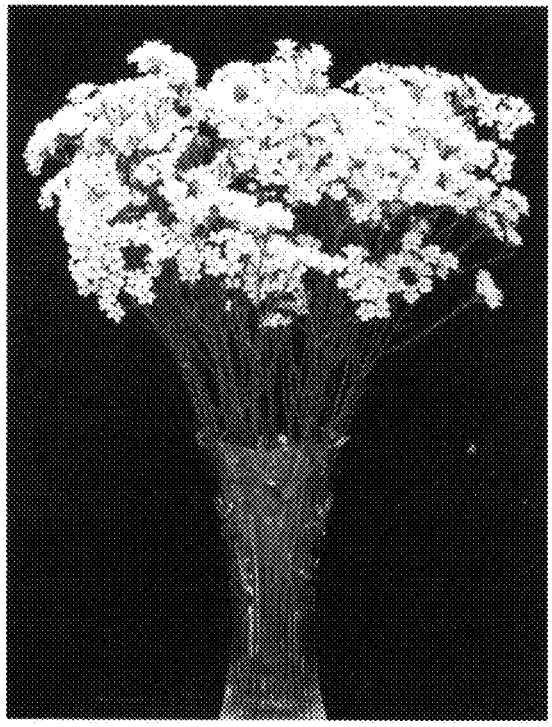
FIG. 3 is a photograph of 'WX 87' flowers.
Figure 4:
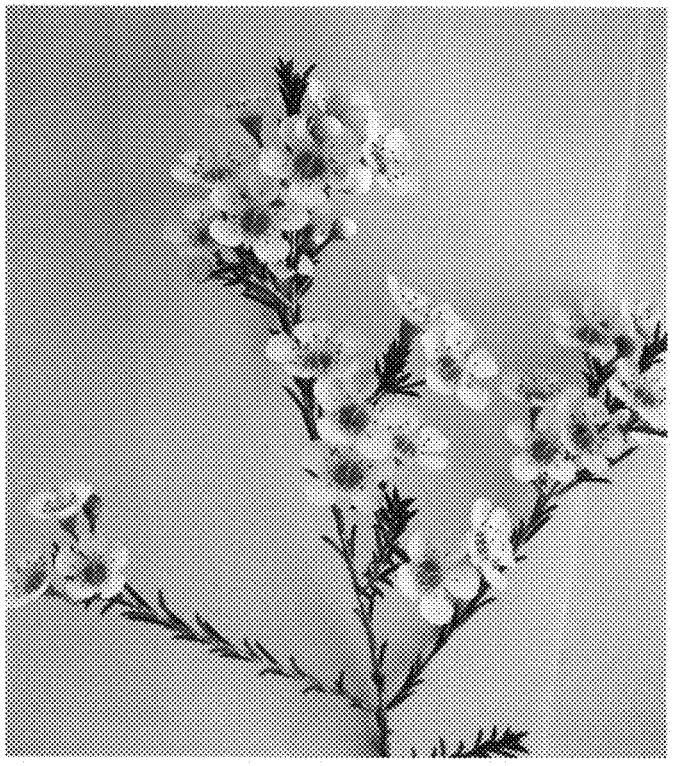
FIG. 4 is a photograph of a branch, leaves and flowers of 'WX 87'.
Figure 5:
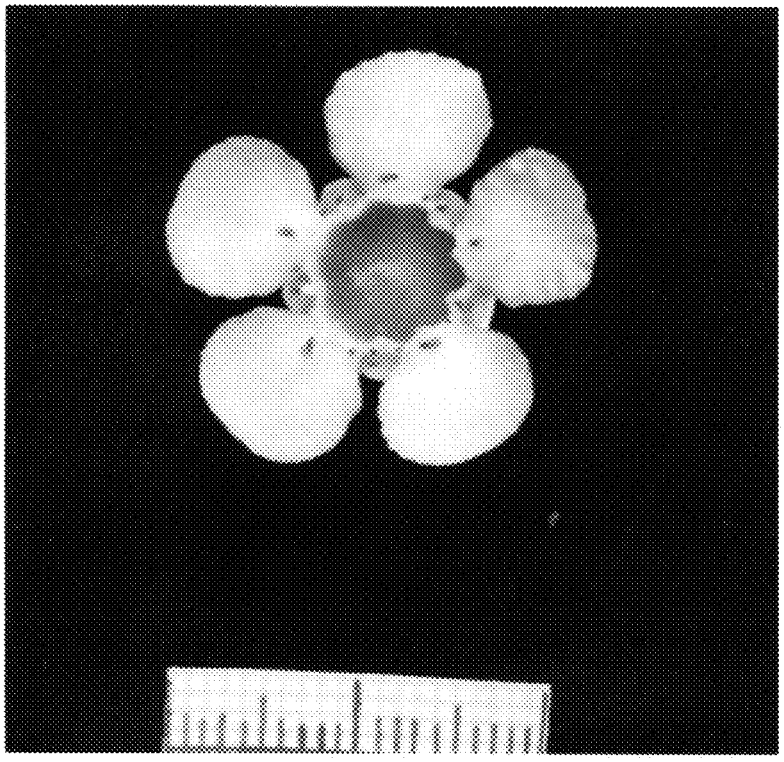
FIG. 5 is a close-up photograph of a flower of 'WX 87' from above.
Figure 6:
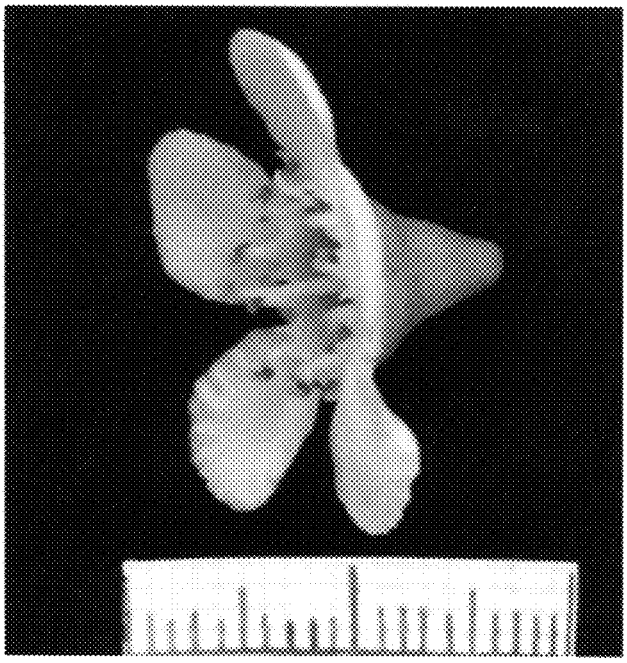
FIG. 6 is a close-up photograph of a flower of 'WX 87' from the side.
Figure 7:
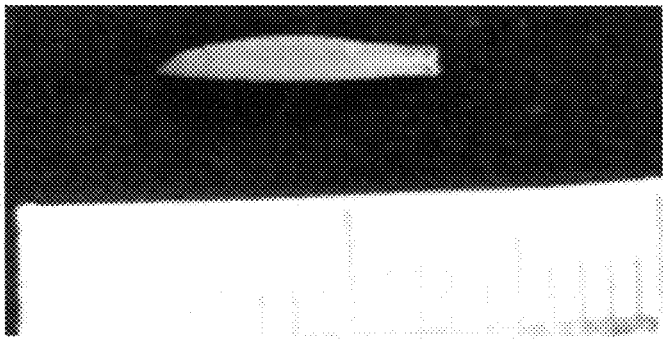
FIG. 7 is a close-up photograph of a leaf of 'WX 87'.
Figure 8:
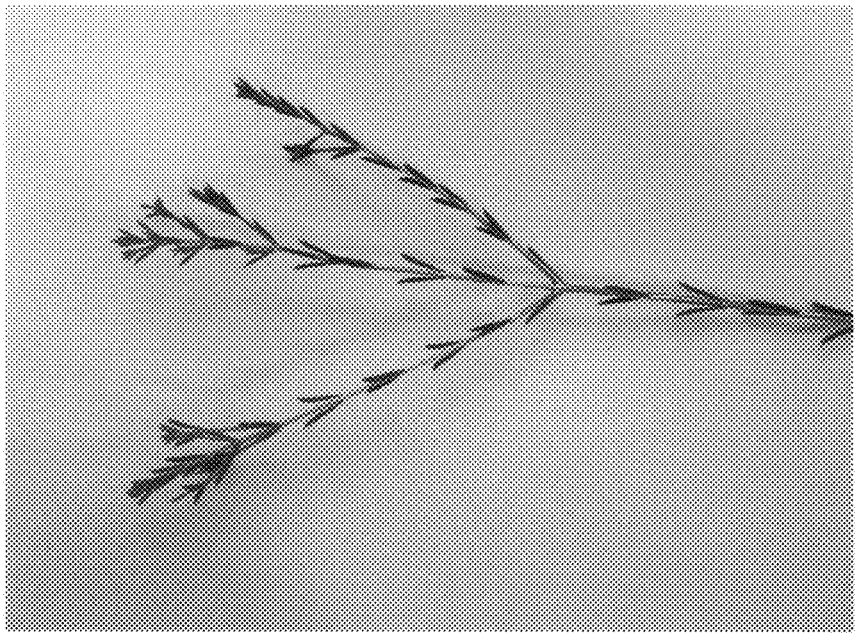
FIG. 8 is a close-up photograph of a branch and leaves of 'WX 87'.
Figure 9:
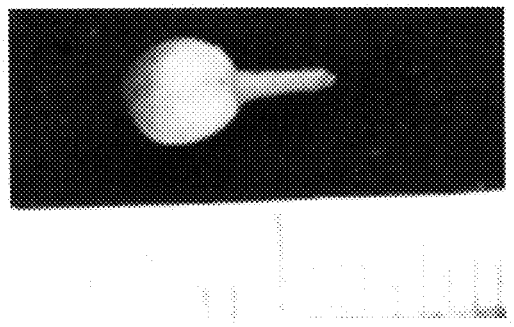
FIG. 9 is a close-up photograph of a young bud of 'WX 87'.
Figure 10:
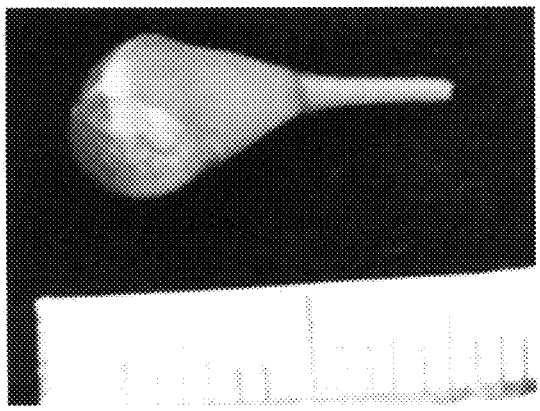
FIG. 10 is a close-up photograph of an older bud of 'WX 87'

The following detailed botanical description is based on observations of four-year-old 'WX 87' waxflower plants growing at Medina, Western Australia during August and September (early spring) 2013, except where otherwise noted. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Plant:

*Summary*.—'WX 87' is a very late flowering, compact, medium-tall bush with dense terminal cover of medium (17 mm) white flowers that age to white.

*Growth habit*.—Branching upright shrub growing to a height of 1.2 m and a bush diameter of 1.2 m.

*Flowering stem length*.—60 cm.

*Branches*.—Average of 20 main branches per plant; diameter 4.6 mm; round cross-section; smooth texture; color Grey-brown 201A and 201C. (Branch description taken from five-year-old stock plants.).

Leaves:

*Leaf arrangement*.—Opposite.

*Leaf density*.—Main branch, about 6 pairs per 6 cm branch length; Secondary branch, 9 pairs of leaves, branch 5 cm in length.

*Attitude*.—Held at about 25 to 30 degree angle to stem.

*Aroma*.—Eucalyptus or citrus aroma when leaves are crushed.

*Leaf internode length*.—Average 16.4 mm on main branch, and 11.1 mm on secondary branch.

*Leaf size*.—Length 11.3 mm, width 1.3 mm.

*Leaf shape*.—Narrowly obovate with acute apex.

*Leaf surface texture*.—Glabrous glandular, leathery, shiny.

*Leaf margin*.—Entire.

*Leaf base*.—Sessile truncate to stem.

*Leaf cross section*.—Triangular with flat upper surface.

*Leaf color*.—New growth, upper and lower surface yellow-green 144B to 144C; mature leaves remain upper and lower surface green N137B.

*Leaf division*.—Simple. Leaf venation — None visible.

Flower:

*Flower bud*.—Fresh buds, cone shaped with smooth shiny surface color yellow-green 145B and tip of bud color orange-red N30; diameter 4.0 mm, length 5.2 mm. Older buds, more elongated with papery operculum, coarse, surface color grey-brown N199B to N199C; diameter 4.4 mm, length 7.2 mm.

*Flowering season*.—Late August to September Medina, Western Australia).

*Flower longevity*.—60 days.

*Flower quality*.—High.

*Flowering time*.—Late to very late.

*Flower description*.—Flowers slightly cupped and petals separate, elongated rounded in shape, upper and lower surface are glabrous waxy, entire margin, truncate base and fused to calyx, rounded apex. Flower color remains constant as it matures (lower and upper surface same coloration).

*Petal color*.—On day of opening white 155A; When partially developed, petals remain white; When fully developed petals remain white NN155B-C.

*Flower arrangement*.—Corymb.

*Flower type*.—Single flower.

*Flowering habit*.—Terminal, panicle florescence.

*Flower shape*.—Cup-shaped.

*Flower diameter*.—Average 17.2 mm; depth 11.5 mm (top of stigma to bottom of ovary).

*Flowering branch angle*.—Small.

*Flowering attitude of petals on day of opening*.—Semi erect.

*Flowering branch angle* 2 *weeks after opening*.—Small.

*Length of sepal in relation to length of petal*.—Less than one-third.

*Petiole* (*pedicle*) *length*.—Long 14.7 mm, aspect 25 degrees to 35 degrees.

*Hypanthium shape*.—Obconical.

*Hypanthium diameter*.—Medium, 7.0 mm.

*Hypanthium main color at middle part on day of opening of flower.*—Green yellow 1A; 4 weeks after opening of flower green-yellow 1B.

*Nectaries.*—About 6 mm in diameter, color see hypanthium.

*Flower petals.*—5, round shape; fused sepals at base to hypanthium, with rounded outer separate lobes arranged alternately between petals; tube portion fluted; fused sepals, white 155A; lobed sepals; new petals white 155A, remaining white NN155B-C as the petals age.

*Petal shape.*—Slightly cupped and undulation of margins weak.

*Petal texture.*—Waxy, glabrous.

*Petal dimensions.*—Similar width (6.7 mm) to length (6.9 mm).

*Stamen collar.*—Color at opening of flower white 155A.

*Stamen collar* 10 *to* 14 *days after opening of flower.*—Color white 155A.

*Gynoecium.*—1 pistil, stigma bearded, color yellow-orange 14D with style white 155A,; length 7.4 mm.

*Androcoecium.*—About 10 fertile stamens with 10 infertile staminodes arranged alternatively on a collar adnate to junction of petals and calyx; filament length 1.8 mm, color white 155A aging to white NN155B-C; staminode length 1.8 mm, color white 155A; anthers length about 0.8 mm, color greyed-orange 166B; pollen is sterile.

Disease resistance: Moderate to high.

I claim:

1. A new and distinct waxflower plant substantially as shown and described herein.

* * * * *